(12) United States Patent
Esmon et al.

(10) Patent No.: US 6,239,101 B1
(45) Date of Patent: May 29, 2001

(54) THROMBIN BINDING POLYPEPTIDES

(75) Inventors: Charles T. Esmon; Naomi L. Esmon, both of Oklahoma City, OK (US); Deborah J. Stearns; Shinichiro Kurosawa, both of Tokyo (JP)

(73) Assignee: Oklahoma Medical Research Foundation, Oklahoma City, OK (US)

(*) Notice: Subject to any disclaimer, the term of this patent is extended or adjusted under 35 U.S.C. 154(b) by 0 days.

(21) Appl. No.: 07/648,900

(22) Filed: Jan. 31, 1991

Related U.S. Application Data

(63) Continuation-in-part of application No. 07/214,774, filed on Jul. 5, 1989, now abandoned.

(51) Int. Cl.[7] .................. C07K 14/745; A61K 38/36; C12N 15/12
(52) U.S. Cl. .................. 514/8; 530/380; 530/350; 530/322; 530/324; 514/12; 435/69.1; 435/69.2; 435/69.6
(58) Field of Search .................. 530/380, 350, 530/324, 322; 514/12, 8; 435/69.1, 69.2, 69.6; 430/250, 10

(56) References Cited

U.S. PATENT DOCUMENTS 4,745,177 * 5/1988 Fritz et al. .................. 530/324

FOREIGN PATENT DOCUMENTS

| WO87/00050 | 1/1987 | (WO) . |
| WO88/09811 | 12/1988 | (WO) . |

OTHER PUBLICATIONS

Creighton, T.E. Proteins: Structure and Molecular Principles W.H. Freeman and Company, New York, 1983, pp. 93–98.*
Rydel et al. 1991. J. Mol. Biol. 221:583–601.*
Ye et al. 1992. J. Biol. Chem. 267(16): 11023–11028.*
Esmon and Owen, Proc.Natl. Acad. Sci. USA 78(4), 2249–2252 (1981).
Esmon, et al., J. Biol. Chem. 257(2), 859–864 (1982a).
Esmon, et al., J. Biol. Chem. 258, 7944–7947 (1982b).
Esmon, et al., J. Biol. Chem. 258, 12238–12242 (1983).
Maruyama, et al., J. Clin. Invest. 75, 987–991 (1985).
Hofsteenge, et al., Biochem. J. 237, 243–251 (1986).
Jakubowski, et al., J. Biol. Chem. 261(8), 3876–3882 (1986).
Kurosawa, et al., J. Biol. Chem. 262(5), 2206–2212 (1987).
Galvin, et al., J. Biol. Chem. 262(5), 2199–2205 (1987).
Kumada, et al., Blood 71(3), 728–733 (1987).
Kurosawa, et al., J. Biol. Chem. 263(13), 5993–5996 (1988).
Bourin, et al., J. Biol.Chem. 263(17), 8044–8052 (1988).
Murata, et al., Thrombosis Res. 50, 647–656 (1988).
Stenflo, et al., J. Biol. Chem. 263(1), 21–24 (1988).

* cited by examiner

Primary Examiner—Keith C. Furman
(74) Attorney, Agent, or Firm—Arnall Golden & Gregory, LLP

(57) ABSTRACT

Small, buffer soluble polypeptides having amino acid structures corresponding to residues 234–486, 310–486, and 407–486, of thrombomodulin and functionally equivalent analogs thereof inhibiting the clotting activity of thrombin and increasing protein C activation. The polypeptides can be coated onto the surface of articles adapted for contacting mammalian blood to render the surface non-thrombogenic. In pharmaceutical compositions, the polypeptides act as a natural anticoagulant.

8 Claims, 7 Drawing Sheets

```
                          245                        262
          234       ┌─────↓──────────────────┬──────────┬──┐
Rabbit e1-TM/  ┌─RW─┤GREAPGAWD?SVG│NGG?EFA??│AS?│GP
         CB1   │HWA─┤REAPGAWDCSVE│NGGCEHACNA│PGA
       Human   │    │                       │    │
       Bovine  └─RWS┤REAPGAWA│CGVE│RGGCQ│RECKGS│ASA│G
                                              H 310                                          339
                ┌──────────────────────────────┬──────────────────┐
         CB2    │?ETGYRV│AADGH│H?EDVDD?AL│VPNP?│PQL
       Human    │CETGYRLAADQHRCEDVDDC│I│LE│PSPC│PQR
       Bovine   │C│EAG│YQ│LAADQHRCEDVDDCAQ│LP│SPC│PQR 418                                    429
                ┌──────────────────────────┬──────┐
         CB3    │FC?│QT│TCPADCDPNYPS│TC│LCPE
       Human    │FCNQTA│CPADCDPN│TQAS│CECPE
       Bovine   │FCNQT│SCPADCDP│HYPTI│CRCPE
         407
```

THROMBIN BINDING POLYPEPTIDES

This is a continuation-in-part of U.S. Ser. No. 07/214,774 filed Jul. 5, 1989, now abandoned, by Charles T. Esmon, Naomi L. Esmon, Deborah J. Stearns, and Shinichiro Kurosawa.

BACKGROUND OF THE INVENTION

The present invention relates generally to synthetic polypeptides, and in particular to peptides having the ability to inhibit the clotting activity of thrombin and to accelerate the activation of protein C, and to peptides having the ability to inhibit the clotting activity of thrombin without accelerating the activation of protein C, all derived from thrombomodulin.

Thrombomodulin is an endothelial cell surface glycoprotein that forms a high affinity complex with thrombin. When thrombin binds to thrombomodulin there is at least a one thousand-fold increase in the activation rate of protein C which forms the anticoagulant enzyme activated protein C. In addition, when thrombin is bound to thrombomodulin, thrombin no longer works as a procoagulant enzyme. Specifically, thrombin-catalyzed fibrin formation, Factor V activation and platelet activation, are all inhibited in the presence of thrombomodulin. Thus, thrombomodulin converts thrombin into a physiological anticoagulant.

Thrombomodulin was first identified in 1980 by C. T. Esmon et al., in a heart perfusion system [Proc. Natl. Acad. Sci. U.S.A., 78:2249–2252 (1981)]. Thrombomodulin has been isolated and purified from rabbit lung [Esmon et al., J. Biol. Chem. 261:859–864 (1982)], from bovine lung [Jakubowski et al., J. Biol. Chem. 261:3876–3882 (1986); Suzuki et al., Biochim. Biophys. Acta, 882:343–352 (1986)], and from human placenta [Salem et al., J. Biol. Chem. 259:12246–12251 (1984); Kurosawa et al., Thromb. Res. 37:353–364 (1985)]. The human thrombomodulin cDNA has been reported providing a structural picture of thrombomodulin. [Suzuki et al., EMBO J. 6:1891–1897 (1987); Wen et al., Biochem. 26:43504357 (1987); Jackman et al., Proc. Natl. Acad. Sci. U.S.A. 84:6425–6429 (1987)]. A partial CDNA sequence of bovine thrombomodulin also has been reported, [Jackman et al., Proc. Natl. Acad. Sci. U.S.A. 82:8834–8838 (1986)], as well as mouse, by Dittman, et al., Nucleic Acids Res. 17:802 (1989).

As the previous reports have shown, the thrombomodulin molecule is organized into five regions: an amino terminal, hydrophobic region, residues 1–244; a cysteine-rich region, residues 245–480; a serine/threonine/proline-rich region with O-glycosylation sites, residues 481–514; a hydrophobic transmembrane region, residues 515–537; and a cytosolic tail containing the remaining 38 residues.

The cysteine-rich region, consisting of the 246 amino acid residues from 234 to 480, has been shown to include six repeated structures homologous to the epidermal growth factor precursor, called EGF-like or EGF-homology domains.

Although human, mouse and bovine thrombomodulin have been studied and characterized with respect to structure and function, the specific functional regions of the thrombomodulin molecule have heretofore remained unknown.

It is therefore an object of the present invention to provide polypeptides derived from regions of thrombomodulin having anticoagulant activity that are suitable for administration to a patient.

It is a further object of the present invention to provide polypeptides which can be used to form non-thrombogenic coatings on the surfaces of medical devices contacting blood.

SUMMARY OF THE INVENTION

Selected polypeptide fragments of the thrombomodulin molecule including residues 234 to 486, 310 to 486 and 407 to 486, respectively, polypeptides comprising amino acid sequences corresponding thereto, and functionally equivalent analogs thereof inhibiting the clotting activity of thrombin and increasing protein C activation, thereby serving as anticoagulants when administered in combination with a pharmaceutically acceptable carrier to a patient, are disclosed. Also disclosed are the use of these polypeptides to coat the surfaces of articles or devices exposed to blood which could otherwise induce clotting.

Methods for using these compositions to inhibit the clotting activity of thrombin without increasing the activation of protein C, and methods to inhibit the clotting activity of thrombin and increase the activation of protein C are also described.

BRIEF DESCRIPTION OF THE DRAWINGS

FIG. 1 shows the amino acid sequence of the amino terminals of el-TM and the CNBr fragments CB1, CB2, and CB3, from rabbit, bovine and human thrombomodulin. The numbering corresponds to human thrombomodulin residues.

FIG. 7A is the rate with thrombin alone (dark circles), and in the presence of CB3 (open circles), and El-TM (triangles).

FIG. 10A is the isolation of CB3; FIG. 10B is the elution of CB3 incubated with N-Glycanase; FIG. 10C is the elution of CB3 that has not been digested with N-Glycanase; and FIG. 10D is the application of the digested CB3 which did not bind to the concanavalin column to a DIP-Thrombin column.

DETAILED DESCRIPTION OF THE PREFERRED EMBODIMENTS

Figure 6:
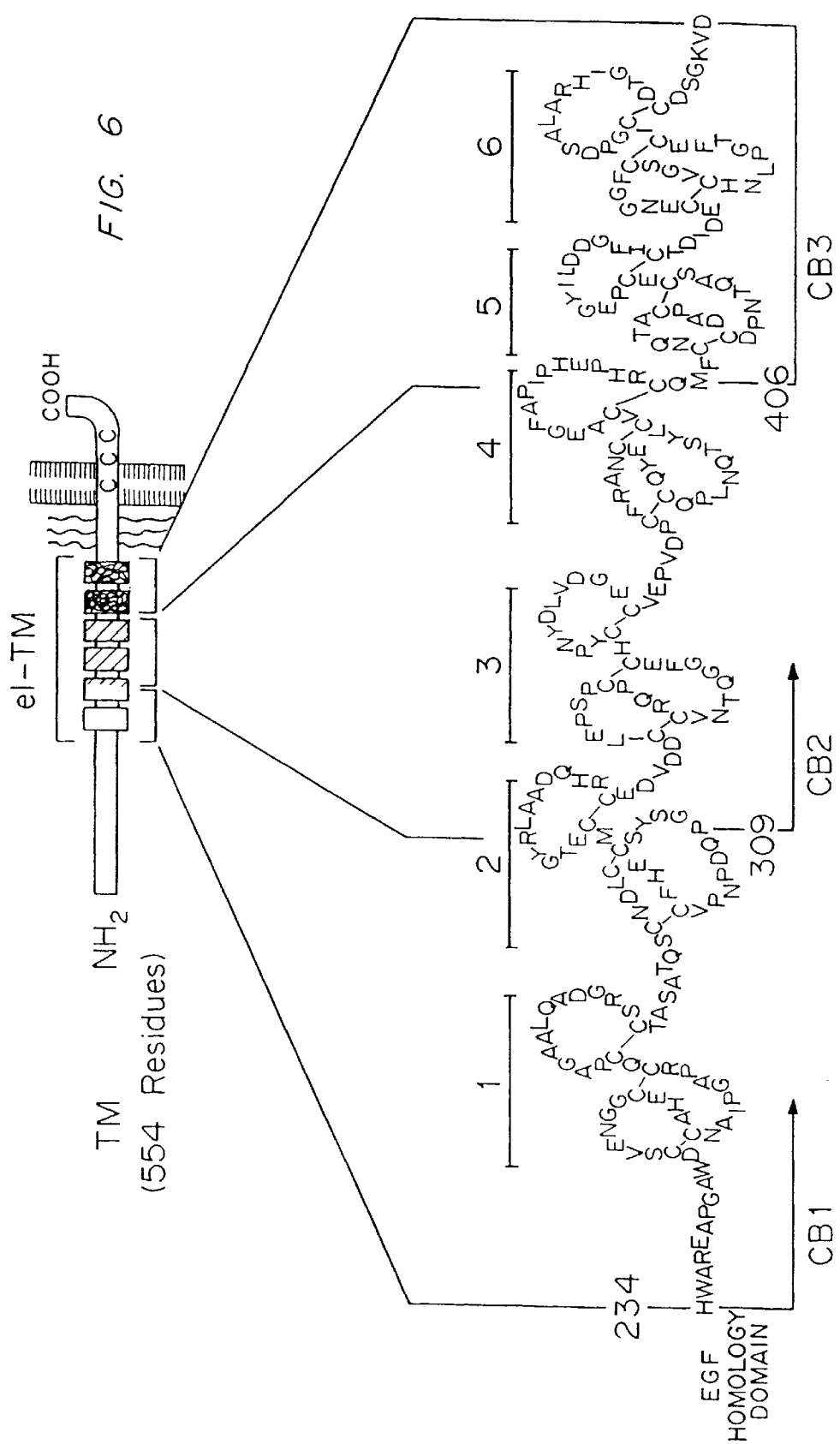
FIG. 6 shows schematically the amino acid structure of human el-TM which corresponds to residues 234 to 486 of thrombomodulin. The CNBr fragments, CB1, CB2 and CB3, begin at residues 234, 310 and 407, respectively.

The studies described herein demonstrate that the functional portions of the thrombomodulin are contained within this region, which is depicted in FIG. 6. More specifically, it has been shown that polypeptides comprising residues 234 to 486 and 310 to 486 have the ability to bind thrombin and significantly increase protein C activation, and that the smaller 80 residue polypeptide comprising residues 407 to 486, though it does not significantly affect protein C activation, does bind thrombin and inhibit its clotting activity.

These functional fragments of thrombomodulin are not species specific. The fragments reacted well with bovine thrombin. Also, amino acid composition analysis and sequencing of these fragments demonstrated a high degree of structural similarity of the cysteine-rich regions in bovine, human and rabbit thrombomodulin. It is therefore not necessary to use a polypeptide structurally identical to the corresponding functional fragment of the species of thrombin with which the polypeptide will be reacted, although in some instances it may be preferable to do so. However, it should be noted that one previous study has been reported as showing that rabbit thrombomodulin has a greater affinity for human thrombin than human thrombomodulin [Kumada et al., Blood 71:728–733 (1987)]. Accordingly, in some applications where the thrombin involved is human, it may be preferred to use polypeptides having the slightly different structure of the rabbit fragment.

Accordingly, the present invention is directed to isolated polypeptides (prepared by enzyme digestion, expression of the appropriate CDNA sequence or synthetically) having structures which correspond to selected fragments of thrombomodulin, namely residues 234 to 486, 310 to 486, and 407 to 486. These fragments will be referred to herein as CB1-2-3 (el-TM), CB2-3, and CB3, respectively, because they were separated by cyanogen bromide digestion.

These polypeptides offer many practical advantages for clinical applications. Because of their relatively small size—253, 177 and 80 residues, respectively—these peptides are much easier to produce. Unlike thrombomodulin, these fragments are buffer soluble, and thus, will be secreted by cells producing them. Also, activity of these fragments is independent of their carbohydrate groups, so they can be efficiently produced by genetically altered bacteria.

Because they are derived from the body's own protein, these polypeptides will not elicit an immune response. Thus, these polypeptides in a pharmaceutical composition provide a natural anticoagulant substance without untoward or adverse side effects common to other anticoagulant drugs, such as heparin, warfarin or hirudin.

A preferred application for the polypeptides is the coating of the surfaces of articles which contact blood, such as artificial valves and hearts, and extracorporeal devices. As described below, the structure of these peptides permits them to be easily linked to synthetic surfaces. Thus, when blood comes in contact with a surface coated with the polypeptides, thrombin will bind to the surface and inhibit clotting thereon, mimicking the natural non-thrombogenic surface of vascular endothelial cells.

Further, it will be appreciated that the smallest of these polypeptides, the 80 residues CB3, has special clinical applications where thrombin binding is required but protein C activation is not. Such a case is disseminated intravascular coagulopathy where the levels of protein C are reduced.

Preparation of the Polypeptides

In accordance with the present invention, there first is prepared a synthetic polypeptide comprising a sequence of amino acid residues corresponding to the sequence of one of the functional fragments of thrombomodulin identified herein. As will be described hereafter, the polypeptides of this invention do not occur naturally, but may be derived from a natural source, namely thrombomodulin, or artificially produced.

The procedures for preparing the polypeptides from thrombomodulin are described herein. It will be appreciated that these polypeptides also may be obtained as a result of genetic engineering. By these techniques, organisms, such as bacteria or mammalian cell lines, are genetically altered to continuously produce a substance they would not naturally produce. These procedures have been published and will not be described in detail herein. Still further, the polypeptides of this invention, having a known amino acid structure, may be manufactured by peptide synthesis. Thus, it will be appreciated that "isolated polypeptides", as used herein, denotes a polypeptide produced by any of these or other techniques.

To prepare these polypeptides from a natural source, thrombomodulin first is isolated and purified from mammalian tissue, and preferably from a human, bovine or rabbit tissue source. One suitable procedure includes isolating thrombomodulin from rabbit lung tissue using detergent extraction and purifying it by using immobilized anti-rabbit thrombomodulin antibodies. This is described by Galvin et al., [J. Biol. Chem., 262:2199–2205 (1987)].

Having obtained substantially pure thrombomodulin, an active elastase proteolytic product, or "el-TM", next may be produced. This may be accomplished by the procedure taught by Kurosawa et al., [J. Biol. Chem. 262:2206–2212 (1987)], which is discussed below in Example 2.

To reduce el-TM to smaller fragments, el-TM may be subjected to cyanogen bromide digestion, as described below in Example 4. The active fragments produced by CNBr digestion then may be identified preferably by applying the digest to a DIP-thrombin column, as described in Example 5 below.

To separate the fragments which bound to the DIP-thrombin column, fragments eluted from the column may be subjected to gel filtration, as described in Example 7 below. This allows separation of el-TM and CB2-3, both of which are capable of activating protein C, from CB3 which is not.

The isolated functional fragments, including CB3, CB2-3, and CB1-2-3 (el-TM), obtained from gel filtration are pooled separately or in a selected combination, and then desalted on a Sephadex G-10 column (0.9 cm,×30 cm, 0.2% N-ethylmorpholine acetate, pH 7.5). The fragments then are lyophilized and stored at 4° C.

Preparation of Coated Articles

The present invention includes an article having one or more of its surfaces coated with a synthetic polypeptide of the present invention, previously described. The coated surface of the article will be relatively non-thrombogenic when contacted with blood because the polypeptides bind thrombin and thereby inactivate the clotting mechanism which otherwise would be triggered on a "foreign" surface.

An article coated with the polypeptide of the present invention is particularly suitable for implantation in a mammal's body. As used herein, implantation may be temporary or permanent, and may involve all or only part of the article. Thus, implantable articles, for purposes of the present invention, include needles, catheters and tubing, as well as artificial valves, vessels and organs.

The lumen of tubes or other conduits used to conduct or contain blood outside the body may be coated with these polypeptides. Preferred applications of this nature would include the conduits used in hemodialysis and heart-lung machines.

For several reasons, the relatively small polypeptides of this invention are better adapted for linkage to artificial surfaces than the larger intact thrombomodulin molecules. First, as mentioned previously, the large membrane spanning domain of thrombomodulin is not buffer soluble, whereas these polypeptides are soluble in buffer solutions. Also, thrombomodulin has no single chemical attachment site, whereas in these smaller polypeptides, attachment is simplified because of the limited number of lysine residues.

Because of the limited number of lysine residues, the coating of the article's surface with the polypeptides of this invention may be carried out by any of several known techniques. Suitable techniques include those which utilize a covalent cross-link between primary amino groups and carboxyl groups, such as corbodiimide cross-linking reactions or hydroxy succinimide reactions. These procedures would be applicable whether the region of the polypeptide being linked corresponded to the amino or carboxy terminus of the smallest CB3 fragment or the larger el-TM elastase product (CB1-2-3).

Another suitable approach to cross-linking involves the substitution of a cysteine residue at appropriate positions in the sequence, typically at or near the amino or carboxy terminus of the EGF domain. This could be accomplished by site-specific mutagenesis of the CDNA or inclusion in chemical synthesis of the polypeptide.

Several techniques have been described for the insertion of a selected residue. One such technique is described by Zoller et al., [Meth. Enzymol., 100:468–500 (1983)], and involves cloning in M13 and then annealling the desired mutation.

With regard to the specific structure of the polypeptide to be used in coating articles, it should be noted that the polypeptides of this invention are not species specific. Thus, for example, a polypeptide having a structure identical to a functional fragment of rabbit thrombomodulin will be effective to bind human thrombin. Indeed, as indicated previously, there is some indication that where the thrombin involved is human, the article preferably will be coated by a polypeptide corresponding to a fragment of rabbit thrombomodulin.

Pharmaceutical Compositions and Treatment Methods

The polypeptides of this invention may be used in pharmaceutical compositions, preferably for intravenous administration. Thus, the above described polypeptides preferably will be combined with an acceptable sterile pharmaceutical carrier, such as five percent dextrose in water, lactated Ringer's solution, normal saline, sterile water, or any other commercially prepared physiological buffer solution designed for intravenous infusion. It will be understood the selection of the carrier solution and the dosage and administration of the composition will vary with the subject and the particular clinical setting, and will be governed by standard medical procedures.

In accordance with the methods of the present invention, these pharmaceutical compositions may be administered in amounts effective, in the case of CB3, to inhibit the clotting activity of thrombin in the subject, and in the case of CB2-3 or CB1-2-3 (el-TM), to increase the activation of protein C as well. Such therapy will be regulated by reference to clotting parameters, such as clotting times, APTTs, fibrinogen levels and platelet counts.

EXAMPLES

The following examples illustrate a method for producing the polypeptides of the present invention and for verifying their activity.

Example 1

Preparation of Purified Thrombomodulin

Thrombomodulin ("TM") in a substantially purified form first was prepared. The protein was isolated from frozen rabbit lung tissue by detergent extraction and purified using an immobilized monoclonal antibody to rabbit thrombomodulin, and affinity chromatography on an immobilized DIP-thrombin column (see Example 5), all as previously described by Galvin, et al., [J. Biol. Chem. 262:2199–2205 (1987)].

Example 2

Preparation of Active Elastase Proteolytic Product of Thrombomodulin

"El-TM", the active elastase proteolytic product of TM, was prepared from the purified rabbit TM, as described by Kurosawa et al., [J. Biol. Chem. 262:2206–2212 (1987)]. The el-TM fragment obtained by this procedure is buffer soluble without detergents, and does not interact with phospholipids. This and the amino acid composition and sequence analysis, described below, indicate that the membrane binding region is lost as a result of the elastase reaction. As reported, the el-TM fragment binds to thrombin, and the el-TM/thrombin complex increases protein C activation significantly.

Example 3

Amino Terminal Sequence Determination of El-TM

Amino acid sequence determinations of el-TM were made using an Applied Biosystems Model 470A gas-phase sequencer equipped with on-line PTH amino acid identification by a Model 120A PTH analyzer (Applied Biosystems, Analytical Division, Santa Clara, Calif.). These determinations were performed by the Molecular Biology Resource Facility of Saint Francis Hospital of the Tulsa Medical Research Institute (Oklahoma City, Okla.).

The results of this analysis are shown in FIG. 1, designated "Rabbit el-TM/CB1". The single letters denote amino acids as follows: alanine, "A"; arginine, "R"; asparagine, "N"; aspartic acid, "D"; cysteine, "C"; glutamic acid, "E"; glutamine, "Q"; glycine, "G"; histidine, "H"; isoleucine, "I"; leucine, "L"; lysine, "K"; methionine, "M"; phenylalanine, "F"; proline, "P"; serine, "S"; threonine, "T"; tryptophan, "W"; tyrosine, "Y"; and valine, "V".

As indicated previously, a partial sequence of the cDNA of bovine thrombomodulin has been reported, allowing the deduction of the amino acid structure of the bovine protein. Also, the amino acid sequence of human thrombomodulin has been deduced from the cDNA of human thrombomodulin. Using this information, the sequence of the amino terminal of the rabbit el-TM fragment was aligned with the bovine and human protein sequences. This revealed that el-TM began at residue 234.

As shown in FIG. 1, the corresponding sections of thrombomodulin are substantially similar. In the figure, identical residues are enclosed. Blanks ("?"), denoting a position held by cysteine residues in the bovine and human thrombomodulin, are enclosed as well. The numbers (234, 245, etc.) corresponds to human thrombomodulin residue numbers.

Example 4

CNBr Digestion of El-TM

El-TM was digested with cyanogen bromide (CNBr) to cleave el-TM at methionine bonds. The general method for CNBr digestions of proteins has been previously described [Steers et al., J. Biol. Chem. 240:2478–2484 (1965)]. To digest el-TM, 1 to 1.3 mg/ml of el-TM dissolved in 70% formic acid was digested with 50 mg/ml CNBr for 24 hours at room temperature. As indicated in Example 9 below, to isolate the larger CB2-3 fragment, the digestion procedure was repeated with a reduced CNBr concentration of 10 mg/ml. The digestion solution was then lyophilized.

Example 5

Selection of CNBr Fragments Which Bound Thrombin

To select those CNBr fragments which possessed the ability to bind thrombin, the digest was applied to a DIP-thrombin column. To prepare this column, bovine thrombin first was purified as described by Owen et al., [J. Biol. Chem. 249:594–605 (1974)]. The purified bovine thrombin was immobilized on an Affi-Gel 10 (Bio-Rad) (0.9×11.5 cm, 5 mg/ml) column and inactivated with diisopropyl fluorophosphate (Behring Diagnostics), as described by Kurosawa et al. [J. Biol. Chem. 262:2206–2212 (1987)]. The column is referred to as a DIP-thrombin column.

The lyophilized CNBr digest was dissolved in 1 ml of 0.1 M NaCl, 0.05 M Tris HCl at a pH of 7.5. The column was equilibrated in 0.1 M NaCl, 0.02 M Tris HCl at a pH of 7.5. This digest solution was then applied into the DIP-thrombin column.

No precipitated material was observed in the sample applied or in the column fractions. 37%–70% of the applied $A_{280}$ did not bind to the column. Unbound fractions were pooled, dialyzed against 0.2% N-ethylmorpholine acetate at a pH of 7.5 and lyophilized.

Bound protein, 31% to 41% of the applied $A_{280}$, was eluted with 2.0 M NaCl, 1.5 M guanidine HCl, 1 mM EDTA, 0.02 M Tris HCl, at a pH of 7.5. Eluted fractions were then desalted on a Sephadex G-10 column (0.9 by 30 cm, 0.2% N-ethylmorpholine acetate, pH 7.5) and lyophilized.

Example 6

Testing of Unbound Fractions for Cofactor Activity

To verify that all the active material had been retained on the column, the unbound or breakthrough fragments from the DIP-thrombin column were tested for the ability to accelerate thrombin-catalyzed protein C activation in 5 mM $Ca^{2+}$. This was done as described by Galvin et al., [J. Biol. Chem. 262:2199–2205 (1987)]. These fractions showed no cofactor activity. 0.2 $A_{280}$ of sample titrated with up to 30 nM thrombin gave ≦0.07 nM activated protein C/min. The breakthrough fractions also did not bind $^{125}$I-thrombin on Western blots.

The identity of these unbound fragments was determined by reverse phase chromatography and amino terminal sequence analysis. The sequence of the unbound fragments corresponded to CB1 and CB2. These sequences are shown in FIG. 1. The methods utilized have been published. [Kurosawa et al., J. Biol. Chem. 263:5993–5996 (1988).

Example 7

Gel Filtration of Bound Fragments

To separate the fragments which bound to the DIP-thrombin column and to provide a preliminary estimate of the sizes of the fragments, the eluted fragments were reconstituted in 3 M guanidine HCl, 0.02 M Tris HCl, pH 7.5, and subjected to gel filtration. Gel filtration was performed on a TSK-125 HPLC column (300×7.5 mm, Bio-Rad) connected to a FPLC pump (Pharmacia LKB Biotechnology Corp.). The column was equilibrated with 3 M guanidine HCl, 0.02 M Tris HCl at a pH of 7.5. The gel filtration standards used were ovalbumin (44 kDa), myoglobin (17.5 kDa), cytochrome c (12.5 kDa) and insulin (5.7 kDa).

Samples of 25 μl each were injected, and 0.5 ml fractions were collected at the rate of 0.7 ml per min. Absorbance was monitored at 280 nm by a Gilson 116 UV Detector.

Figure 2:
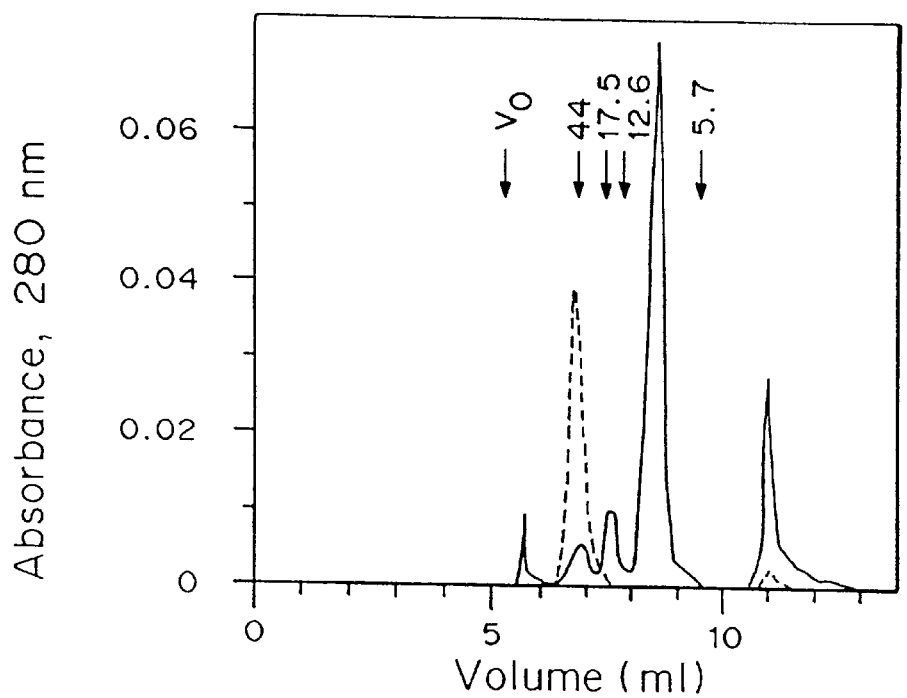
FIG. 2 is a graph of gel filtration of the CNBr fragments capable of binding to thrombin in solid lines and el-TM in dotted lines.

The results of the gel filtration are shown in FIG. 2. The dotted lines show the chromatogram of el-TM which eluted as a 49 kDa protein. The arrows show the elution volumes of the four standards, and their known molecular masses are adjacent to the arrows.

One major peak and four minor peaks were observed. Molecular masses in kDa were calculated graphically from the elution volumes according to a standard curve of log molecular mass of standards versus Ve/Vo where Ve=elution volume and Vo=void volume, here 5.32 ml. The major peak corresponded to 10 kDa. Four other minor peaks were observed, and these corresponded to $V_o$, 45 kDa, 29 kDa, and $V_1$, respectively.

Example 8

Reverse Phase Chromatography of the Smallest Thrombin-binding Fragment (CB3)

The major peak from the gel filtration column, which corresponded to 10 kDa protein or CB3, was further analyzed by reverse phase chromatography. This verified purity of the preparation.

Figure 3:
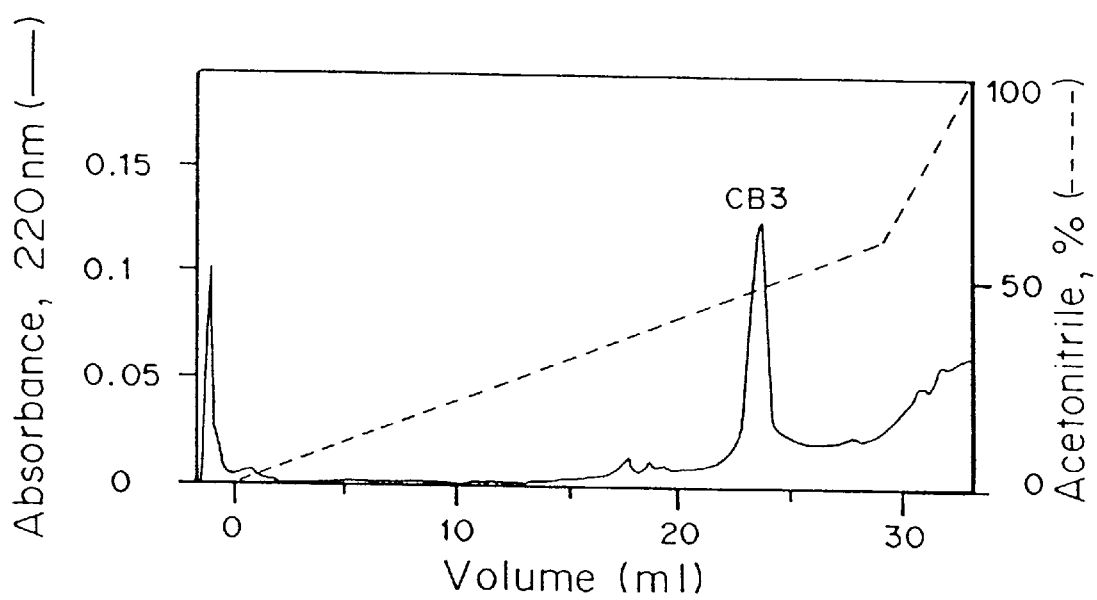
FIG. 3 is a graph of reverse phase chromatography performed on CB3.

For this, a Pro RPC 5/10 $C_1$–$C_8$ column (Pharmacia LKB Biotechnology, Inc.) was used. The column was equilibrated with 0.1% trifluoroacetic acid in water. Samples of the 10 kDa protein from the TSK-125 column (see filtration) were reconstituted in 0.1% trifluoroacetic acid in water in a total volume of 50 μl. These samples were injected onto the column and eluted with a linear gradient of acetonitrile in 0.1% trifluoroacetic acid at the rate of 0.2 ml/min. The results of the reverse phase chromatography of the 10 kDa fragment is shown in FIG. 3.

Example 9

Isolation of 29 kDa CNBr Fragment

The 29 kDa CNBr fragment, or CB2-3, was isolated in a manner essentially identical to that for the CB3 fragment except that the CNBr concentration was decreased to 10 mg/ml, as detailed in Example 4. The method involves CNBr digestion, affinity chromatography of the digest on a DIP-thrombin column and gel filtration of the thrombin-binding species on a TSK-125 column, all as described above.

The TSK-125 column was equilibrated in 3 M guanidine HCl, 0.02 M Tris HCl at a pH of 7.5. The lyophilized DIP-thrombin eluate was dissolved in 200 μl of the same guanidine buffer and injected onto the column. The flow rate was 0.7 ml/min and 0.25 ml fractions were collected, as depicted in FIG. 4.

To assay for cofactor activity, 20 μl of these fractions were each diluted 1:1,000 in 0.1 M NaCl, 0.1% gelatin, 0.02 M Tris HCl at a pH of 7.5. These were incubated with 1 μM protein C, 10 nM thrombin and 5 mM $CaCl_2$ for 20 min. at 37° C. The reaction was terminated by the addition of antithrombin III to a final concentration of 7.1 μM. Activated protein C then was assayed as described by Galvin et al., [J. Biol. Chem. 262:2199–2205 (1987)].

Figure 4:
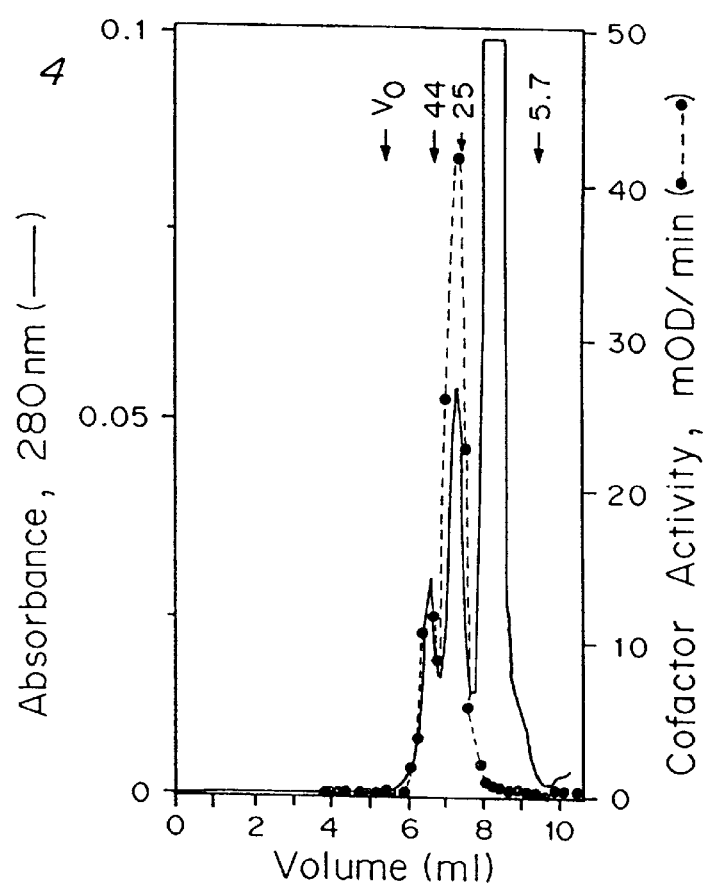
FIG. 4 is a graph of gel filtration for the isolation of CB2-3.

As shown in FIG. 4, there are two distinct peaks of cofactor activity. The first peak is associated with the 45 kDa material, which is residual el-TM from the CNBr digestion. The second peak of activity is associated with the 29 kDa material. The third large $A_{280}$ absorbing peak without any cofactor activity is the CB3 fragment.

Example 10

Determination of Amino Terminal Sequence of CB3 Fragment

Samples of CB3 from the reverse phase columns (section 8 above), were reduced and carboxyamidomethylated, as shown in Example 12, and subjected to amino terminal sequence analysis, as described above in Example 3. The determined sequence then was compared to the deduced known sequences of human and bovine thrombomodulin, and this is shown in FIG. 1. CB3 begins at residue 407.

Example 11

Determination of Amino Terminal Sequence of CB2-3

The determination of the amino terminal sequence of the CB2-3 fragment was carried out essentially as described for el-TM (Example 3) and CB3 (Example 10). Samples. of CB2-3 from the gel filtration chromatography described above were prepared for sequencing by suspending them in a solution of 4 M guanidine HCl, 1 mM EDTA and 0.1 M Tris HCl at a pH of 8.5. These were reduced with dithiothreitol (Calbiochem) with a 50 fold molar excess over cysteines at 37° C. for 3 hours under $N_2$. Iodoacetamide (Sigma) was added at a 2.6 fold molar excess over the dithiothreitol and this solution was incubated at 37° C. for 2 hours under $N_2$.

Excess reagents in this solution were removed by reverse phase chromatography on an HPLC Econosphere-300 $C_4$ column (4.6×250 mm from Alltech Associates, Inc.). This column was equilibrated in 0.1% trifluoroacetic acid in water. The material was eluted with a 0%–70% linear gradient of acetonitrile in 0.1% trifluoroacetic acid at a flow rate of 1 ml/min and detection at 220 nm.

Then, the amino terminal sequence of the peptide was determined, as described above in Example 3. The results of the amino terminal sequence analysis demonstrated that CB2-3 begins at residue 310 and was identical to that previously observed for CB2 (Example 6).

The molecular size of this fragment (29 kDa), its amino terminal sequence and its ability to bind to the DIP-thrombin column demonstrated that it contained both CB2 and CB3, wherein el-TM was cleaved with CNBr only after the residue 309. This active fragment is called CB2-3.

Example 12

Amino Acid Composition Analysis

CB3 fragment, suspended in a solution of 4 M guanidine HC1, 1 mM EDTA and 0.1 M Tris HCl at a pH of 8.5, was reduced with dithiothreitol (Calbiochem) with a 50 fold molar excess over cysteines at 37° C. for 1 hour under $N_2$. Iodoacetamide (Sigma) was added at 2.6 fold molar excess over the dithiothreitol. This solution was incubated at 37° C. for 1 hour under $N_2$.

For CB3, excess reagents were removed by reverse phase chromatography on a HPLC $C_3$ column having dimensions of 4.6 mm×75 mm (Beckman Instruments of Berkeley, Calif.). The column was equilibrated in 0.1% trifluoroacetic acid (Pierce) in water.

The sample then was eluted with a 0% to 50% linear gradient of acetonitrile in 0.1% trifluoroacetic acid (Burdick and Johnson Laboratories). The eluent then was subjected to acid hydrolysis in 6 N HCL for 24 hours in a vacuum at 110° C.

The amino acid composition was determined using a Dionex D-500 amino acid analyzer according to the manufacturer's directions. The amino acid analysis was also performed by the Molecular Biology Resource Facility. The results for CB3 are shown below in Table I.

For CB2-3, the sample was prepared for amino acid composition analysis in the same manner as for sequencing as described above in Example 11. The remainder of the analysis procedure for CB2-3 was carried out in the same manner as above for CB3. The results of the CB2-3 analysis are shown in Table II.

The amino acid composition for CB2-3 was calculated both on the basis of the 26 predicted cysteine residues and assuming a total of 177 residues. The composition fit better the predicted composition when it was based on the 177 residues suggesting slight incomplete reduction and carboxyamidomethylation.

TABLE I

Comparison of the amino acid composition of the thrombin binding domain of rabbit TM with the 5th and 6th EGF-like regions of TM.

| Residue | Rabbit[a] | Human[b] | Bovine[b] |
| --- | --- | --- | --- |
| CM-Cysteine | 12.2 | 12 | 12 |
| Aspartic Acid | 11.6 | 12[c] | 11[c] |
| Threonine | 4.6 | 5 | 6 |
| Serine | 5.3 | 3 | 4 |
| Glutamic Acid | 10.1 | 7[d] | 7[d] |
| Proline | 8.2 | 5 | 7 |
| Glycine | 6.3 | 8 | 7 |
| Alanine | 2.9 | 5 | 2 |
| Valine | 1.8 | 1 | 0 |
| Methionine | 0 | 0 | 0 |
| Isoleucine | 2.7 | 5 | 8 |
| Leucine | 4.4 | 3 | 2 |
| Tyrosine | 4.5 | 1 | 3 |
| Phenylalanine | 0.9 | 4 | 1 |
| Histidine | 0 | 2 | 2 |
| Lysine | 0 | 0 | 0 |
| Arginine | 1.1 | 1 | 1 |
| Tryptophan | ND[e] | 0 | 0 |
| TOTAL Residues | 76.6 | 74 | 73 |

[a]Amino acid composition of CNBr fragment of rabbit el-TM after 24 hour acid hydrolysis.
[b]Calculated from the cDNA sequences of human TM reported by Suzuki, et al., EMBO J. 6, 1891–1897 (1987); Wen, et al., Biochemistry 26, 4350–4357 (1987); and Jackman, et al., Proc. Natl. Acad. Sci. USA 84, 6425–6429 (1987) and bovine TM, reported by Jackman, et al., Proc. Natl. Acad. Sci. USA 84, 6425–6429 (1987). Includes residues Phe 40-Cys 480, according to the numbering of human TM used by Wen, et al., and Jackman, et al.
[c]Includes aspartic acid and asparagine residues.
[d]Includes glutamic acid and glutamine residues.
[e]Not determined.

TABLE II

Comparison of the amino acid composition of the active CNBr fragment with thrombomodulin residues 310–486.

| Residue | Rabbit[a] | Human[b] | Bovine[b] |
| --- | --- | --- | --- |
| CM-Cysteine | 26.0 (22.6) | 26 | 26 |
| Aspartic Acid | 29.1 (25.4) | 24[c] | 25[c] |
| Threonine | 8.9 (7.8) | 7 | 9 |
| Serine | 7.1 (6.2) | 6 | 6 |
| Glutamic Acid | 27.0 (23.5) | 23[d] | 24[d] |
| Proline | 21.5 (18.7) | 15 | 17 |

TABLE II-continued

Comparison of the amino acid composition of the active CNBr fragment with thrombomodulin residues 310–486.

| Residue | Rabbit[a] | Human[b] | Bovine[b] |
|---|---|---|---|
| Glycine | 19.8 (17.3) | 14 | 15 |
| Alanine | 9.7 (8.4) | 10 | 9 |
| Valine | 10.4 (9.1) | 8 | 8 |
| Methionine | 0.7 (0.6) | 1 | 1 |
| Isoleucine | 3.7 (3.2) | 7 | 9 |
| Leucine | 12.4 (10.8) | 8 | 5 |
| Tyrosine | 9.7 (8.4) | 6 | 6 |
| Phenylalanine | 6.7 (5.8) | 7 | 4 |
| Histidine | 4.5 (3.9) | 6 | 6 |
| Lysine | 0.5 (0.4) | 1 | 2 |
| Arginine | 4.6 (4.0) | 6 | 4 |
| Tryptophan | ND[e] (ND) | 0 | 0 |
| TOTAL Residues | 204 (177) | 177 | 176 |

[a]Amino acid composition of the active CNBr fragment of rabbit el-TM after 24 hour acid hydrolysis. composition was calculated to give the best fit to integral values for each amino acid assuming either 26 CM-Cys residues or, in ( ), a total of 177 residues.
[b]Calculated from the cDNA sequences of human TM reported by Suzuki, et al., EMBO J. 6, 1891–1897 (1987); Wen, et al., Biochemistry 26, 4350–4357. (1987); and Jackman, et al., Proc. Natl. Acad. Sci. USA 84, 6425–6429 (1987) and bovine TM, reported by Jackman, et al., PNAS USA 84, 6425–6429 (1987). Includes residues Cys 310-Asp 486, according to the numbering of human TM used by Wen, et al., and Jackman, et al.
[c]Includes aspartic acid and asparagine residues.
[d]Includes glutamic acid and glutamine residues.
[e]Not determined.

Example 13

Identification of the Carboxy Terminus of CB3 (and CB2-3 and El-TM)

The carboxy terminus of CB3, which provided by inference the carboxy terminus of CB2-3 and el-TM, was then determined. Reduced, carboxyamidomethylated CB3 was incubated with TPCK-trypsin since CB3 contains one arginine residue and no lysine residues. A peptide isolated from the digest was sequenced and found to begin at residue 457 (an asparagine) in the sixth EGF-like region (FIG. 6). The entire peptide was sequenced: Asn$^{457}$-Leu-Pro-Gly-Ser-Tyr-Glu-CM/Cys-Ile-CM/Cys-Gly-Pro-Asp-Ser -Pro-Leu-Ala-Gly-Gln-Val-Ser-Thr-Glu-CM/Cys-Tyr-Pro-Thr-Gln-Val-Ser$^{486}$. The bold residues (Asn$^{457}$-Leu-Pro-Gly-, Tyr-Glu-CM/Cys, Pro-Thr-Gln-Val) are identical to bovine TM; underlined residues are identical with human TM. The last residue of this rabbit peptide, serine (486), is a predicted elastase cleavage site, suggesting that this residue is the carboxy terminal residue of CB3, CB2-3 and el-TM. The 80 residue peptide predicted from the sequence determination is consistent with the reported amino acid composition of CB3 (Table I) which yielded an estimated 77 total residues.

Example 14

Testing the CB3 Fragment for Cofactor Activity

The CB3 (10 kDa) fragment was tested for the ability to activate human protein C, according to the procedure described by Galvin et al., (J. Biol. Chem. 262:2199–2205 (1987)] using 1 µM human protein C obtained as described by Vigano-D'Angelo et al., [J. Clin. Invest., 77:416–425 (1986)]. The cofactor activity of CB3 (per mole) was found to be 0.06% of the activity of el-TM. It was concluded that the CB3 fragment alone was not sufficient for significant activation of protein C, even though it did bind thrombin.

Example 15

Testing the CB3 Fragment for Ability to Inhibit Protein C Activation

Figure 5:
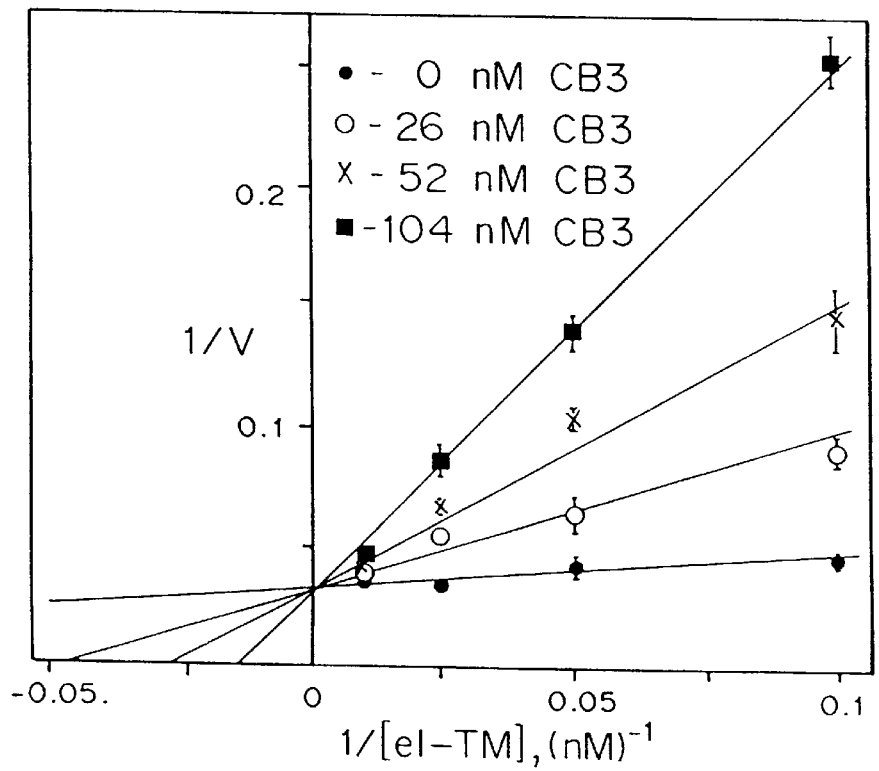
FIG. 5 is a graph of the ability of CB3 at four different concentrations (0 nM CB3, dark circle), 26 nM CB3, open circle, 52 nM CB3, X, and 104 nM CB3, dark square) to compete with el-TM for the binding site on thrombin.

The ability of CB3 to inhibit the rate of protein C activation was measured by examining the capacity of CB3 to inhibit el-TM/thrombin catalyzed protein C activation. Protein C (1 µM) was activated at 37° C. in a solution of 0.1 M NaCl, 0.1% gelatin, 5 mM $Ca^{2+}$, 0.02 M Tris HCl at pH 7.5 and containing 0.16 nM bovine thrombin. Activation was tested at four concentrations of CB3: 0 nM, 26 nM, 52 nM and 104 nM and variable concentrations of el-TM as indicated in FIG. 5. After 20 minutes, the reactions were stopped by additions of antithrombin III (7.1 µM) and assayed as described by Galvin et al., [J. Biol. Chem. 262:2199–2205 (1987)]. The results are shown in FIG. 5.

In FIG. 5, the bars represent the standard deviation of triplicate determinations. Nonlinear regression analysis of the data was performed with a Hewlett Packard 9826A computer using programs for analysis of competitive and noncompetitive inhibition, as described by Cleland [Adv. Enzymol. Relat. Areas Mol. Biol. 29:1–32 (1967)]. Analysis indicated that inhibition was competitive in nature with respect to el-TM.

Example 16

Measurement of the Ability of CB3 and El-TM to Inhibit Clotting Activity of Thrombin As shown, CB3 does not accelerate protein C activation. To determine if this fragment inhibited thrombin clotting of fibrinogen, fibrin formation was monitored by fibrinopeptide release in the presence and absence of CB3.

The fibrinogen used was human fibrinogen purified from human plasma and was free of fibronectin and Factor XIII. It was received from Dr. Bunei Ando of the Oklahoma Medical Research Foundation (Oklahoma City, Okla.). Sodium dodecyl sulfate polyacrylamide electrophoresis under reducing conditions showed only protein bands corresponding to the α, β and gamma chains of fibrinogen. The fibrinogen was dialyzed against 0.1 M NaCl, 0.1% polyethylene glycol 6000, 0.02% $NaN_3$, 0.02 M Tris HCl, pH 7.5 and stored at −80° C.

Human fibrinogen (0.1 mg/ml) was mixed with each of 50 nM el-TM and 50 nM CB3 in 0.1 M NaCl, 0.1% polyethylene glycol 6000, 0.02% $NaN_3$, 0.02 M Tris HCl, pH 7.5 at 37° C. In a third mixture neither el-TM nor CB3 was added. Bovine thrombin (0.2 nM final concentration) was added to start the reaction, for a total volume in each sample of 0.5 ml. At the times indicated in FIG. 7, 50 µl samples were removed and added to diisopropyl fluorophosphate (final 40 mM). These samples were assayed for fibrinopeptide A ("FPA") and fibrinopeptide B ("FPB") content by chromatography on an HPLC $C_{18}$ column as described below.

For each experiment, the total release of fibrinopeptides was determined by incubating fibrinogen (0.1 mg/ml) with 10 nM thrombin for 60 min. at 37° C. The clot was wound onto a glass rod and the supernatant was assayed for fibrinopeptide content. The peak areas of FPA and FPB obtained under these conditions was considered to be 100%. A standard curve (peak area versus nmoles FPA or FPB) was constructed from the results of an incubation of 4.4 µM fibrinogen and 7 nM thrombin (90 min., 37° C.). The experimental values for the total release samples were always within 10%–14% of the predicted values by reference to the standard curve.

For separation of fibrinopeptides, 25 µl samples were injected onto a Vydac HPLC $C_{18}$ column (10 micron, 4.6×259 mm). The buffers contained 10 mM $KH_2PO_4$ at a pH of 5.8. For buffer A, the buffer contained 2% acetonitrile, and for buffer B, the buffer contained 25% acetonitrile.

The gradient profile has been published:
0 min: 75% buffer A, 25% buffer B
10 min: 56% buffer A, 44% buffer B
20 min: 30% buffer A, 70% buffer B

[Hofsteenge, et al., Biochem. J. 237:243–251 (1986). The flow rate was 1 ml/min and peptides were detected at 215 nm. The chromatograms were essentially identical to that previously reported. Fibrinopeptide A typically eluted at 11.9 min and fibrinopeptide B at 18.7 min.

Figure 7A:
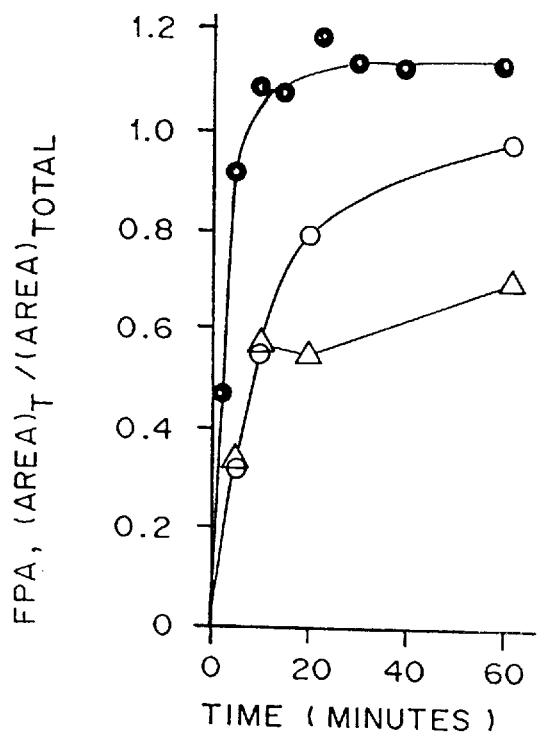
FIGS. 7A and B depicts the rate of release of fibrinopeptides (FPA, $(Area)_T/(Area)_{Total}$, FIG. 7A, FPB, $(Area)_T/(Area)_{Total}$, FIG. 7B) over time (minutes) by thrombin in the presence of CB3 and el-TM.
Figure 7B:
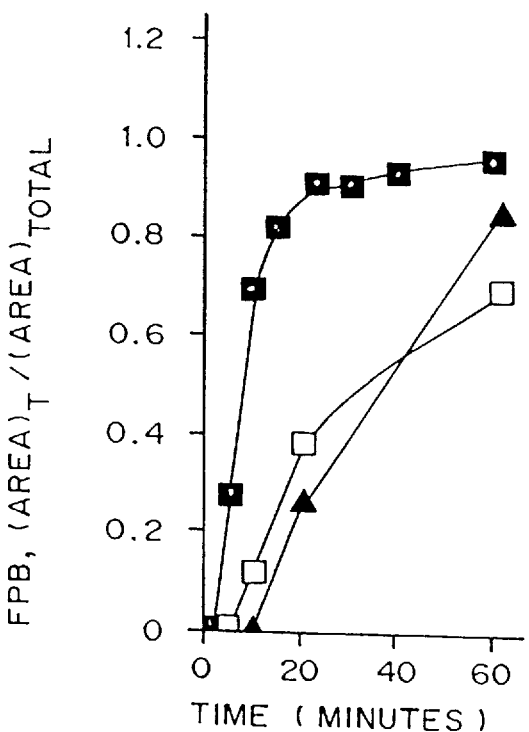
FIG. 7B is the rate with thrombin alone (dark squares), and in the presence of CB3 (open squares) and El-TM (dark triangles).

The data from these experiments is depicted in the graphs shown in FIGS. 7A and 7B, and are expressed as the ratio of the FPA or FPB peak area at time T relative to the peak area determined from the total reaction mixture. This data shows both el-TM and CB3 inhibit the rate of release of fibrinopeptides from fibrinogen by thrombin. Thus, the clotting activity of thrombin is diminished in the presence of these fragments.

Example 17

Thrombin Titration of CB2-3 for Kd Determination

Human protein C (1 µM) was incubated with 2 nM el-TM and with CB2-3 separately, each reaction being carried out at 37° C. in 0.1 M NaCl, 0.1% gelatin, 5 mM CaCl$_2$, 0.02 M Tris HCl, at a pH of 7.5. The reactions were started by the addition of thrombin (final 0–100 nM). The solutions were incubated for 7 min. and the reaction stopped by addition of antithrombin III to 7.1 µM. Activated protein C then was assayed as described by Galvin et al., [J. Biol. Chem. 262:2199–2205 (1987)].

The Kd determined on duplicate samples of two separate preparations of CB2-3 was 13.2±2.4 nM and 8.9±0.9 nM. The Kd determined for el-TM was 7.4±2.7 nM (duplicates on one preparation). The Kd values were quantified by nonlinear regression analysis of the data, assuming a 1:1 stoichiometry in the complex and after correction for bound thrombin, using Enzfitter software (Elsevier Science Publishers BV, Amsterdam, the Netherlands).

Figure 8:
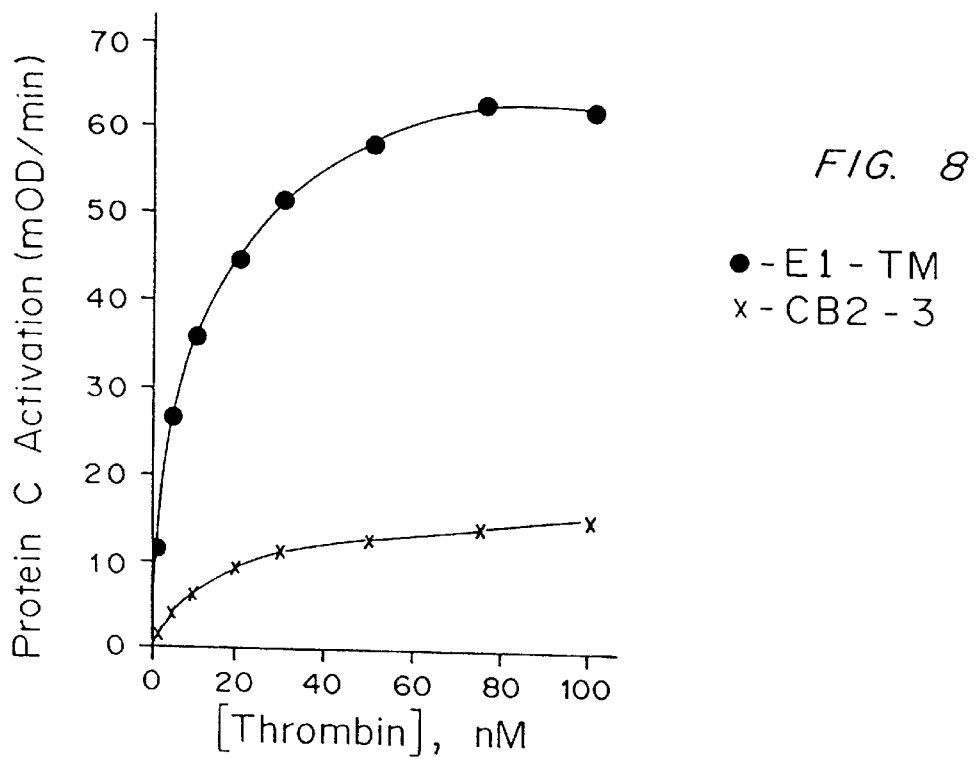
FIG. 8 is a graph of protein C activation (absorbance/min) versus thrombin concentration (nM) used to determine the Kd of El-TM (dark circles) and CB2-3 (X).

The results are shown in FIG. 8. As shown, CB2-3 is capable of supporting protein C activation. The Kd for thrombin is similar to that observed for el-TM. However, the maximum rate of activation by the CB2-3/thrombin complex is significantly lower.

Example 18

Protein C Titration of CB2-3 for Km Determination

CB2-3 and el-TM, each at a final concentration of 80 nM, were incubated at 37° C. with 0–10 µM human protein C in 0.1 M NaCl, 0.1% gelatin, 0.3 mM Cacl$_2$, 0.02 M Tris HCl, pH 7.5. Thrombin (0.1 nM final) was added and the solution incubated for 8 min. The reaction was terminated by addition of antithrombin III to 7.1 µM. Activated protein C was assayed as previously described by Galvin et al., [J. Biol. Chem. 262:2199–2205 (1987)].

Figure 9:
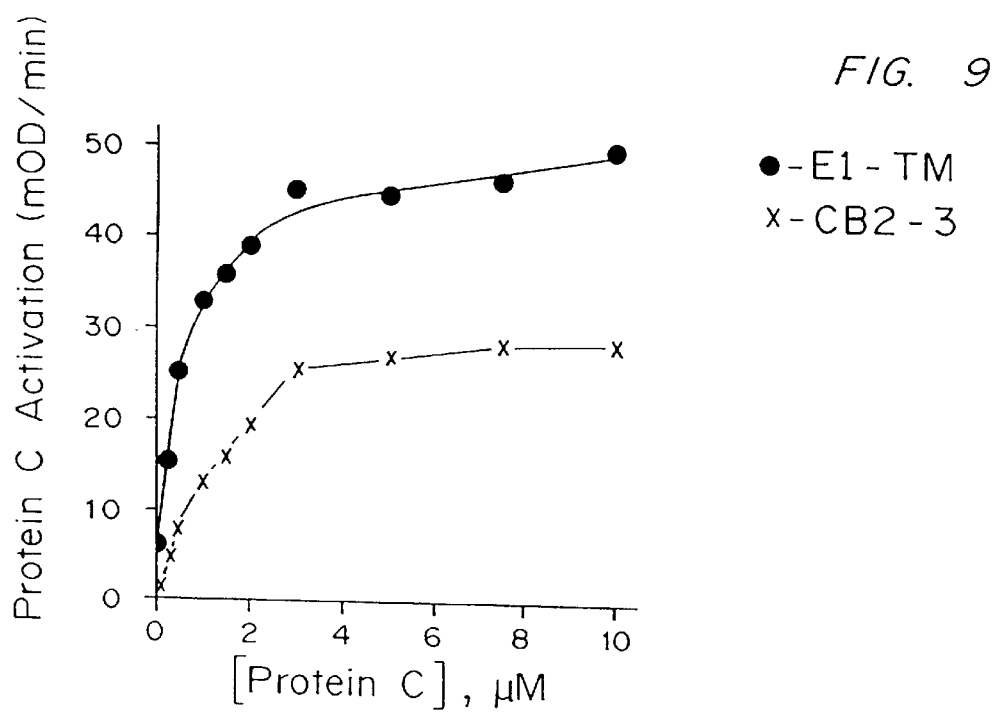
FIG. 9 is a graph of protein C activation (absorbance/min) versus protein C concentration ($\mu$M) used to determine the Km of El-TM (dark circles) and CB2-3 (X).

The Km determined on two separate preparations of CB2-3 was 1.9±0.3 µM and 1.6±0.2 µM. The Km determined on a single preparation of el-TM was 0.8±0.009 µM. The Km values were determined by nonlinear regression analysis of the data using the software identified above. The calculated kcat for the CB2-3 preparations were: 103 and 159 mol/min/mol, respectively. For el-TM, kcat was 212 mol/min/mol. The results are shown in FIG. 9.

Example 19

Demonstration that N-linked Oligosaccharides on CB3 are not Required for Thrombin Binding Based on the observation that position 409 in CB3 consistently gave a blank cycle in sequencing and that the Asn-X-Thr sequence (a consensus sequence for N-glycosylation) was conserved among species, there was reason to believe CB3 was glycosylated. To determine if this moiety was required for thrombin binding, CB3 was deglycosylated.

Figure 10A:
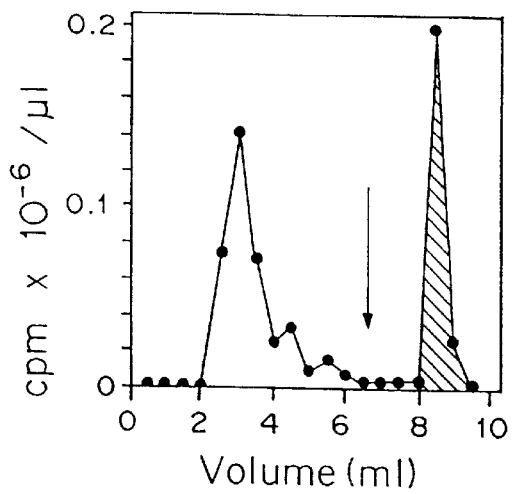
FIGS. 10A–D are the elution profiles of deglycosylated CB3 on Concanavalin-A (A–C) and DIP-thrombin (D) columns.

CB3 was iodinated using Enzymobeads (Bio-Rad) according to the manufacturer's instructions. $^{125}$I-CB3 (4.5× 10$^9$ cpm) was applied to a 2 ml concanavalin A lectin column (Pharmacia LKB Biotechnology Corp.) (6.18 mg protein/ml) equilibrated in 0.1 M NaCl, 1 mM CaCl$_2$, 0.02 M Tris HCl, pH 7.5 (0.5 ml/min, 0.25 ml fractions). Bound $^{125}$I-CB3 was eluted with 0.5 M ethyl-α-D-mannopyranoside (Sigma), indicated by the arrow in FIG. 10A. The eluted peak fraction (hatched area) was dialyzed against 0.1 M NaCl, 0.1 M Tris HCl, pH 8.6. The $^{125}$1-CB3 was detected by counting the fractions in a gamma counter.

50 µl of the dialyzed material was incubated overnight at 37° C. with final concentrations of 120 U/ml N-Glycanase (Genzyme Company of Boston, Mass.), 10 mM 1,10 phenanthroline, 0.03 M NaCl, 0.1 M Tris HCl, pH 8.6 in a total volume of 150 µl. A control tube with $^{125}$I-CB3 but without the N-Glycanase was incubated in parallel. These samples were reapplied to 2 ml concanavalin A columns using the same conditions as above.

Figure 10C:
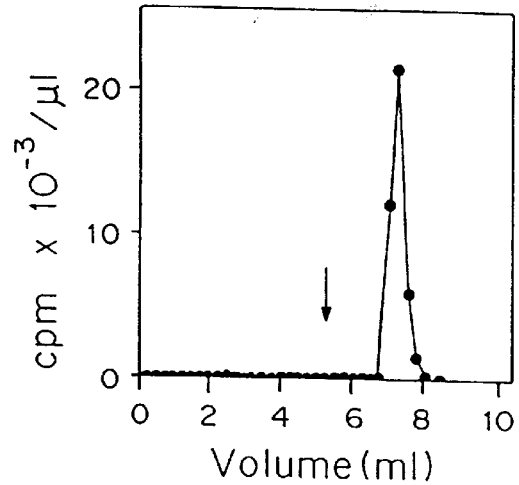
Figure 10B:
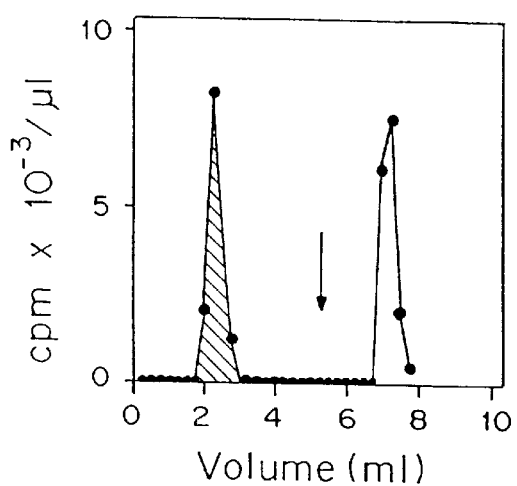
Figure 10D:
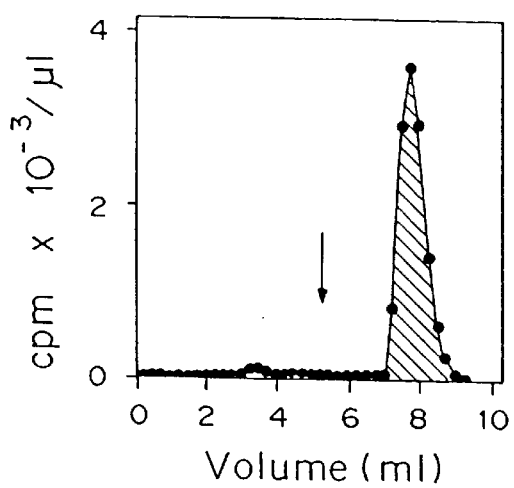

Shown in FIG. 10B is the data from the sample eluted shown in 10A and treated as above with N-Glycanase. FIG. 10C shows the control sample without N-Glycanase. Depicted in FIG. 10D is data from the application of the N-Glycanase treated CB3 which no longer bound to the Con A column (the hatched peak in FIG. 10B) to a DIP-thrombin column (0.9×11 cm, 0.5 ml/min, 0.25 ml fractions). The column was equilibrated in 0.1 M NaCl, 0.02 M Tris HCl, pH 7.5. Bound deglycosylated $^{125}$I-CB3 was eluted with 2 M NaCl, 1.5 M guanidine HCl, 5 mM EDTA, pH 7.5. This is indicated by the arrow in FIG. 10D.

These data show that the N-linked oligosaccharide present on CB3 is not required for the peptide to bind thrombin. Thus, genetically altered bacteria, which cannot produce carbohydrates, can be employed to produce the polypeptides of this invention.

Changes may be made in the nature, composition, operation and arrangement of the various elements, steps and procedures described herein without departing from the spirit and scope of the invention as defined in the following claims.

We claim:

1. A polypeptide consisting essentially of an amino acid sequence which corresponds to residues 407 to 486 of a mammalian thrombomodulin as shown in FIG. 6.

2. The polypeptide of claim 1, wherein the amino acid sequence corresponds to residues 407 to 486 of a thrombodulin isolated from an animal selected from the group consisting of human, rabbit, and bovine.

3. The polypeptide of claim 1 having the formula:

Phe Cys Asn Gln Thr Ala Cys Pro Ala Asp Cys

Asp Pro Asn Thr Gln Ala Ser Cys Glu Cys Pro

Glu Gly Tyr Ile Leu Asp Asp Gly Phe Ile Cys

Thr Asp Ile Asp Glu Cys Glu Asn Gly Gly Phe

Cys Ser Gly Val Cys His Asn Leu Pro Gly Thr

Phe Glu Cys Ile Cys Gly Pro Asp Ser Ala Leu

Ala Arg His Ile Gly Thr Asp Cys Asp Ser Gly

Lys Val Asp.

4. The polypeptide of claim 1 prepared by proteolytic and chemical cleavage of thrombomodulin.

5. The polypeptide of claim 1, synthesized chemically.

6. A pharmaceutical composition comprising an amount of the polypeptide of claim 1 effective to inhibit coagulation in a mammalian subject in need thereof and a pharmaceutically acceptable carrier.

7. A pharmaceutical composition comprising an amount of the polypeptide of claim 3 effective to inhibit coagulation in a mammalian subject in need thereof and a pharmaceutically acceptable carrier.

8. A method for inhibiting coagulation in a mammalian subject in need thereof comprising administering to the subject an effective amount of an isolated polypeptide consisting essentially of an amino acid sequence which corresponds to residues 407 to 486 of a mammalian thrombomodulin as shown in FIG. 6 in combination with a pharmaceutically acceptable carrier, to inhibit the clotting activity of thrombin without increasing protein C activation.

* * * * *